US010435354B2

(12) United States Patent
Heilig et al.

(10) Patent No.: US 10,435,354 B2
(45) Date of Patent: *Oct. 8, 2019

(54) PROCESS FOR PREPARING ISOCYANATES IN DIALKYL CARBONATES AS SOLVENT

(71) Applicant: BASF SE, Ludwigshafen (DE)

(72) Inventors: Manfred Heilig, Speyer (DE); Thomas Schulz, Dresden (DE); Torsten Mattke, Freinsheim (DE); Filip Nevejans, St. Gillis-Waas (CN); Kai Thiele, Antwerp (BE); Stefan Maixner, Schwetzingen (DE)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/057,482

(22) Filed: Aug. 7, 2018

(65) Prior Publication Data

US 2018/0346414 A1    Dec. 6, 2018

Related U.S. Application Data

(63) Continuation of application No. 15/305,923, filed as application No. PCT/EP2015/058550 on Apr. 21, 2015, now Pat. No. 10,093,615.

(30) Foreign Application Priority Data

Apr. 23, 2014  (EP) .................................... 14165533

(51) Int. Cl.
*C07C 263/10*  (2006.01)
(52) U.S. Cl.
CPC ................................ *C07C 263/10* (2013.01)

(58) Field of Classification Search
None
See application file for complete search history.

(56) References Cited

U.S. PATENT DOCUMENTS

| | | | |
|---|---|---|---|
| 3,465,021 A | 9/1969 | Twitchett | |
| 10,093,615 B2 * | 10/2018 | Heilig | ................... C07C 263/10 |
| 2006/0252960 A1 | 11/2006 | Sohn | |

FOREIGN PATENT DOCUMENTS

| | | |
|---|---|---|
| DE | 844 896 | 9/1952 |
| GB | 1037933 | 8/1966 |
| GB | 1146664 | 3/1969 |
| WO | WO 99/54289 A1 | 10/1999 |

OTHER PUBLICATIONS

International Search Report dated Jul. 10, 2015 in PCT/EP2015/058550 (submitting English translation only).
International Preliminary Report on Patentability dated Mar. 29, 2016 in PCT/EP2015/058550 (submitting English translation only).
Carl Hanser Verlag, Polyurethane, Kunststoff Handbuch, vol. 7, 3$^{rd}$ revised edition, 1993, pp. 76-88.
Werner Siefken, Mono-und Polyisocyanate, Justus Liebigs Annalen Der Chemie, 562, 1949, pp. 75-136.

* cited by examiner

*Primary Examiner* — Amy C Bonaparte
(74) *Attorney, Agent, or Firm* — Oblon, McClelland, Maier & Neustadt, L.L.P.

(57) ABSTRACT

The invention relates to a process for preparing isocyanates by reacting primary amines with phosgene in a solvent, where the solvent comprises a dialkyl carbonate.

9 Claims, No Drawings

PROCESS FOR PREPARING ISOCYANATES IN DIALKYL CARBONATES AS SOLVENT

CROSS-REFERENCE TO RELATED APPLICATIONS

This application is a continuation application of Ser. No. 15/305,923, filed Oct. 21, 2016, pending, which is a National Stage application of PCT/EP2015/058550, filed Apr. 21,2015 and which claims benefit of priority from EP 14165533.2, filed Feb. 24, 2003, the entire contents of each of which are incorporated herein by reference.

DESCRIPTION

The invention relates to a process for preparing isocyanates by reacting primary amines with phosgene in a solvent.

The preparation of isocyanates from amines and phosgene is known. Depending on the type of amines, the reaction is carried out either in the gas phase or in the liquid phase, both batchwise and continuously (W. Siefken. Liebigs Ann. 562, 75 (1949)). The continuous preparation of organic isocyanates by reaction of primary organic amines with phosgene has been described many times and is carried out on an industrial scale (see Ullmanns Enzyklopädie der Technischen Chemie, volume 7 (Polyurethane), 3rd revised edition, Carl Hanser Verlag, Munich-Vienna, p. 76ff (1993)). The aromatic isocyanates TDI (tolylene diisocyanate) and MDI (methylenediphenyl diisocyanate), PMDI (polymethylenepolyphenylene polyisocyanate) and mixtures of MDI and PMDI and also the aliphatic isocyanates HDI (hexamethylene diisocyanate) and isophorone diisocyanate (IPDI), in particular, are prepared industrially.

Present-day industrial syntheses of the aromatic diisocyanates MDI and TDI and the aliphatic diisocyanates HDI and IPDI are carried out virtually exclusively in continuous processes. A continuous process for carrying out the reaction in a plurality of vessels through which continuous flow occurs is described, for example, in DE 844 896. In general, the continuous embodiment of the process has two stages. In the first stage of the phosgenation, the amine is reacted with phosgene to form the corresponding carbamoyl chloride and hydrogen chloride and the amine hydrochloride. The reaction between amine and phosgene is very fast, strongly exothermic and proceeds even at very low temperatures. To minimize by-product and solids formation, amine and phosgene, both optionally with an organic solvent, therefore have to be mixed quickly, for which reason the first phosgenation stage is generally carried out in a mixing device, preferably in a nozzle. The second stage of the phosgenation comprises both the decomposition of the carbamoyl chloride into the desired isocyanate and hydrogen chloride and also the phosgenation of the amine hydrochloride to form the carbamoyl chloride. The temperature in the second phosgenation stage is generally higher than in the first.

As solvents, use has hitherto been made of chlorinated aromatic hydrocarbons such as dichlorobenzene, chlorobenzene, trichlorobenzene or mixtures thereof, aromatic or aliphatic hydrocarbons such as toluene, xylene, benzene, pentane, hexane, heptane, octane, cyclohexane, biphenyl, ketones such as 2-butanone, methyl isobutyl ketone, esters such as diethyl isophthalate, ethyl acetate, butyl acetate, nitriles such as acetonitrile and also sulfolane. However, the isocyanate yields achieved here are still capable of improvement.

It is an object of the invention to provide an improved process for preparing isocyanates by reacting primary amines with phosgene in the liquid phase.

It has surprisingly been found that dialkyl carbonates are particularly well suited as solvents for the phosgenation of primary amines to isocyanates. Experiments have shown that higher isocyanate yields are achieved in dialkyl carbonates as solvents than in other solvents, for example in chloroaromatics. A higher isocyanate yield is also achieved in mixtures of dialkyl carbonates and chloroaromatics. This is all the more surprising because a person skilled in the art would have expected that primary amines would react with dialkyl carbonates to form urethanes, as a result of which the isocyanate yield would have to be decreased.

As an alternative to achieving a higher isocyanate yield, it is also possible to work at a lower excess of phosgene or at a lower dilution while achieving the same isocyanate yield.

The invention accordingly provides a process for preparing isocyanates by reacting primary amines with phosgene in a solvent, wherein the solvent comprises a dialkyl carbonate.

Suitable dialkyl carbonates are symmetrical or unsymmetrical di-$C_1$-$C_6$-alkyl carbonates. Preferred dialkyl carbonates are dimethyl carbonate, diethyl carbonate, di-n-propyl carbonate and diisopropyl carbonate.

The dialkyl carbonate can be present in admixture with a further solvent. Suitable further solvents are chlorinated aromatic hydrocarbons such as monochlorobenzene, dichlorobenzene, trichlorobenzene or mixtures thereof, aromatic or aliphatic hydrocarbons such as toluene, xylene, benzene, pentane, hexane, heptane, octane, cyclohexane, biphenyl, ketones such as 2-butanone, methyl isobutyl ketone, esters such as diethyl isophthalate, ethyl acetate, butyl acetate, nitriles such as acetonitrile and also sulfolane.

Preferred further solvents are chlorinated aromatic hydrocarbons such as monochlorobenzene, dichlorobenzene, trichlorobenzene or mixtures thereof. Preference is given to monochlorobenzene and o-dichlorobenzene. The further solvents can be present in amounts of from 10 to 90% by weight, preferably from 10 to 50% by weight, based on the sum of solvents (dialkyl carbonates plus further solvents).

Preferred solvent mixtures comprise from 50 to 100% by weight of dialkyl carbonate, preferably diethyl carbonate, and from 0 to 50% by weight of chlorinated aromatic hydrocarbons, particularly preferably monochlorobenzene and/or o-dichlorobenzene.

Preferred primary amines which are reacted in the process of the invention are toluenediamine (TDA), diphenylmethanediamine (MDA) and polymethylenepolyphenylenepolyamine (PMDA). These are converted by the process of the invention into tolylene diisocyanate (TDI), methylenediphenylene diisocyanate (MDI) and polymethylenepolyphenylene polyisocyanate (PMDI), respectively. Further primary amines which can be reacted by means of the process of the invention are isophoronediamine, hexamethylenediamine or 1,5-naphthalenediamine, which are converted into isophorone diisocyanate (IPDI), hexamethylene diisocyanate (HDI) and 1,5-naphthalene diisocyanate, respectively.

In a preferred embodiment of the process of the invention, the reaction is carried out in at least two stages, with the first stage being carried out in a mixing device and the second stage being carried out in at least one residence apparatus. These two stages can be followed by a third stage which is carried out in at least one materials separation apparatus. For example, the preparation of methylene diisocyanate (MDI) is preferably carried out in two stages, but can also be carried out in three stages. The preparation of tolylene diisocyanate is generally carried out in three stages. The pressure in each successive stage is preferably lower than in the preceding stage.

In the first stage of the process of the invention, the reaction of the amine to form carbamoyl chloride and amine hydrochloride essentially occurs, in the second stage the reaction of the amine hydrochloride formed in the first stage to form carbamoyl chloride essentially occurs and in the third stage the dissociation of the carbamoyl chloride into isocyanate and hydrogen chloride essentially occurs. In the first stage, the premixed feed stream comprising the amine and solvent or solvent mixture and the phosgene-comprising feed stream, which can additionally comprise hydrogen chloride and/or solvent, are mixed, with mixing of the feed streams generally being carried out very quickly.

Here, the reaction between organic amine and phosgene is carried out in two, three or more stages in dialkyl carbonate as inert solvent using a phosgene excess of generally from 1 to 1000%, preferably from 50 to 450% excess over the stoichiometric amount of phosgene, with a reduction in the pressure occurring in each of the stages. The first phosgenation stage comprises a static mixer, preferably a nozzle. The pressure upstream of the nozzle is preferably from 3 to 70 bar, in particular from 15 to 45 bar. The pressure difference over the nozzle is at least 0.5 bar. The temperature in the first stage is preferably from 80 to 190° C., in particular from 90 to 150° C. The second stage comprises one or more residence apparatuses, preferably one residence apparatus, which is operated at a pressure of from 1.5 to 35 bar, preferably from 2 to 25 bar. Downstream of the nozzle, depressurization to the pressure of the residence apparatus of the second stage is carried out by means of a valve or another device suitable for this purpose. However, the natural pressure drop through the nozzle can also be used for pressure reduction.

The reactor of the first stage can also be integrated into the reactor of the second stage. In particular, a mixing nozzle can dip into the gas phase or preferably into the liquid phase of the second reactor, i.e. can be present entirely or partly therein. The output from the nozzle can also be conveyed by means of a pipe, an immersed tube or a plug-in tube into the gas phase or preferably into the liquid phase of the reactor of the second stage.

The temperature in the second stage is generally from 80 to 190° C., preferably from 90 to 150° C. Possible types of reactor for the second stage are tube reactors, stirred vessels, unstirred residence apparatuses, phase separation apparatuses and other apparatuses. The reactor can have a heatable reactor wall or an internal heat exchanger. The reactor can also be provided with a pumped circuit which can in turn comprise a heat exchanger for adjusting the reactor temperature. In the case of a stirred vessel, an unstirred residence apparatus or optionally also in the case of a phase separation apparatus, the liquid phase is preferably depressurized under level regulation into the reactor of the third stage and the gas phase is preferably depressurized under pressure regulation into the reactor of the third stage. However, the gas phase, comprising mainly phosgene, hydrogen chloride and possibly solvent, can also be conveyed directly to the work-up, e.g. fractionation into phosgene, hydrogen chloride and solvent or into mixtures thereof. The residence reactor of the second stage can, depending on the desired residence time and capacity of the plant, have larger dimensions and volumes, which can be disadvantageous from cost or safety aspects, e.g. phosgene holdup at high pressure. In this case, the reactor of the second stage can also be formed by two or more identical or different reactors and reactor types which can be connected in parallel or, optionally to influence the residence time spectrum, also in series.

The reactor of any third stage present in the process of the invention is operated at a pressure of from 1.5 to 20 bar, preferably from 2 to 16 bar. Downstream of the residence reactor of the second stage, depressurization is carried out to the pressure of the third reactor by means of a valve or another device suitable for this purpose. A natural pressure drop can optionally also be utilized.

The temperature in the third stage is generally from 80 to 190° C. As reactor type for the third reactor, use is made of a column, in particular a reaction column, as is described, for example, in WO 99/54289. The temperature at the bottom is generally from 80 to 190° C. and the temperature at the top is from 50 to 120° C. The column used as reactor of the third stage can also be utilized for removing the excess phosgene from the reaction mixture. In order that the reactor of the third stage is not disadvantageously large, the reactor of the third stage can also be made up of two or more identical or different columns connected in series.

The output from the bottom of the reaction column is worked up by conventional methods to remove any phosgene still present and to separate off the solvent. In the case of the preparation of TDI, the crude TDI is subsequently subjected to a removal of high boilers and pure distillation. From the vapors from the reaction column and optionally the residence reactor of the second stage, phosgene, hydrogen chloride and optionally solvent are separated off in a known way and optionally recirculated.

The invention is illustrated by the following examples.

EXAMPLES

Example 1 (Comparative Example)

1300 g of monochlorobenzene and 130 g of phosgene were placed in a thermostated stirred vessel at 50° C. A mixture of 100 g of PMDA and 1300 g of monochlorobenzene was metered into the initial charge via an immersed tube over a period of 1 hour, with the temperature being maintained at 50° C. The gas phase was conveyed via a dry ice condenser with reflux into a scrubbing column. After the metered addition was complete, the reaction mixture was heated to about 120° C. and parts of the solvent and residual phosgene were subsequently evaporated. Solvent residues were subsequently separated off from the remaining reaction mixture in a rotary evaporator under reduced pressure (50 mbar), firstly at 100° C. and subsequently at 180° C., in each case for one hour. The NCO number of the sample (proportion by weight of NCO groups in the sample) was subsequently determined by means of titration as a measure of the yield and found to be 31.8% by weight.

Example 2 (According to the Invention)

The above-described experiment was repeated with a mixture of 520 g of diethyl carbonate and 780 g of monochlorobenzene being used instead of 1300 g of monochlorobenzene in the initial charge. The NCO number determined was 32.2% by weight.

The invention claimed is:

1. A process for preparing isocyanates, the process comprising reacting at least one primary amine with phosgene in at least one solvent, to obtain at least one isocyanate, wherein:

the solvent comprises a dialkyl carbonate;

the reacting occurs in at least two stages, with a first stage being carried out in a mixing device and a second stage being carried out in at least one residence apparatus; and the first stage occurs at a temperature of from 80 to 190° C.

2. The process according to claim 1, wherein the dialkyl carbonate is selected from the group consisting of dimethyl carbonate, diethyl carbonate, di-n-propyl carbonate and diisopropyl carbonate.

3. The process according to claim 1, wherein the dialkyl carbonate is present in admixture with a further solvent.

4. The process according to claim 3, wherein the further solvent comprises an aromatic chlorinated hydrocarbon.

5. The process according to claim 4, wherein the aromatic chlorinated hydrocarbon is selected from the group consisting of monochlorobenzene and o-dichlorobenzene.

6. The process according to claim 4, wherein the solvent comprises from 50 to less than 100% by weight of diethyl carbonate and from greater than 0% to 50% by weight of the aromatic chlorinated hydrocarbon as the further solvent, based on a weight sum of the dialkyl carbonate and the further solvent.

7. The process according to claim 1, wherein the at least one primary amine is selected from the group consisting of toluenediamine (TDA), diphenylmethanediamine (MDA), a polymethylenepolyphenylenepolyamine (pMDA), isophoronediamine, hexamethylenediamine and 1,5-naphthalenediamine.

8. The process according to claim 1, wherein the reaction is carried out in at least three stages, with a third stage being carried out in at least one materials separation apparatus and the pressure in each successive stage being lower than in the preceding stage.

9. The process according to claim 3, wherein the further solvent consists of at least one aromatic chlorinated hydrocarbon.

* * * * *